United States Patent [19]
Berman et al.

[11] Patent Number: 5,312,621
[45] Date of Patent: May 17, 1994

[54] METHOD OF TREATING FIBROTIC DISORDERS

[75] Inventors: Brian Berman, Orinda; Matthew R. Duncan, Concord, both of Calif.

[73] Assignee: Baker Cummins Dermatologicals, Inc., Miami, Fla.

[21] Appl. No.: 871,280

[22] Filed: Apr. 20, 1992

Related U.S. Application Data

[63] Continuation of Ser. No. 469,149, Jan. 24, 1990, abandoned, which is a continuation-in-part of Ser. No. 147,973, Jan. 25, 1988, abandoned.

[51] Int. Cl.$^5$ .................. A61K 37/66; C12P 21/06; C07K 3/00; C07H 15/12
[52] U.S. Cl. .................. 424/85.7; 424/85.4; 424/85.6; 435/69.5; 435/69.51; 530/350; 530/351; 536/22.1; 536/23.2
[58] Field of Search .................. 424/85.4, 85.6, 85.7; 530/350, 351; 536/22.1, 23.2; 435/69.5, 69.51

[56] References Cited

PUBLICATIONS

Jimenez et al. "Selective Inhibition of Human Diploid . . . " J. Clin. Invest. 74:1112–1116 (1984).
Duncan et al. "γ Interferon is the Lymphokine . . . " J. Exp. Med. 162:516–527 (1985).
Wickramasinghe et al. "γ-Interferon in Primary . . . " Lancet 2:1524–1525 (1987).

*Primary Examiner*—Charles L. Patterson, Jr.
*Assistant Examiner*—Hyosuk Kim
*Attorney, Agent, or Firm*—Kirschstein, Ottinger, Israel and Schiffmiller

[57] ABSTRACT

A novel method of treating fibrotic disorders in humans comprises the administration of a sufficient quantity of a composition containing a human alpha- or beta-interferon to raise the total concentration of such interferon in the affected tissue area to about 10 to about $4 \times 10^7$ IU per cubic centimeter. The interferons used can be naturally derived or recombinant DNA-derived. The interferon composition can be administered by any indicated conventional method and can include any pharmaceutically acceptable, interferon-compatible vehicle.

10 Claims, 8 Drawing Sheets

FIG. 3

| FIBROBLAST | | ³H-COLLAGEN (DPM / 10³ CELLS ± SD) IN VITRO | | | |
|---|---|---|---|---|---|
| SOURCE | PASSAGE | UNTREATED | IFN-α2b 10⁵ U/ml | IFN-α2b 10³ U/ml | IFN-α2b 10 U/ml |
| KELOID PRE - IN VIVO IFN- | 2 | 96 ± 7 | 48 ± 5 | 64 ± 4 | 89 ± 15 |
| KELOID POST - IN VIVO IFN- | 1 | 59 ± 5 | 34 ± 2 | 44 ± 3 | 51 ± 1 |
| NORMAL SKIN UNTREATED | 1 | 56 ± 5 | 23 ± 5 | 33 ± 1 | 49 ± 1 |
| KELOID PRE - IN VIVO IFN- | 6 | 93 ± 14 | 55 ± 2 | NT | NT |
| KELOID POST - IN VIVO IFN- | 5 | 36 ± 3 | 25 ± 5 | NT | NT |
| NORMAL SKIN UNTREATED | 5 | 50 ± 9 | 28 ± 1 | NT | NT |
| KELOID PRE - IN VIVO IFN- | 7 | 107 ± 6 | 43 ± 4 | NT | NT |
| KELOID POST - IN VIVO IFN- | 6 | 33 ± 6 | 24 ± 4 | NT | NT |
| NORMAL SKIN UNTREATED | 6 | 52 ± 6 | 29 ± 1 | NT | NT |

Table I. Effect of *in vivo* and *in vitro* Treatment with Interferon-α2b on Collagen Production by Dermal Fibroblasts

| FIBROBLAST | | $^3$H-GLYCOSAMINOGLYCAN (DPM / 10$^3$ CELLS ± SD) | | | |
| --- | --- | --- | --- | --- | --- |
| | | IN VITRO | | | |
| SOURCE | PASSAGE | UNTREATED | IFN-α2b 10$^5$ U/ml | IFN-α2b 10$^3$ U/ml | IFN-α2b 10 U/ml |
| KELOID PRE-IN VIVO IFN- | 3 | 122 ± 15 | 56 ± 3 | 83 ± 5 | 120 ± 13 |
| KELOID POST-IN VIVO IFN- | 2 | 78 ± 9 | 71 ± 3 | 69 ± 1 | 83 ± 13 |
| NORMAL SKIN UNTREATED | 2 | 80 ± 6 | 47 ± 2 | 59 ± 1 | 78 ± 6 |
| KELOID PRE-IN VIVO IFN- | 7 | 92 ± 1 | 61 ± 3 | NT | NT |
| KELOID POST-IN VIVO IFN- | 6 | 62 ± 7 | 58 ± 5 | NT | NT |
| NORMAL SKIN UNTREATED | 6 | 65 ± 3 | 47 ± 5 | NT | NT |

Table II. Effect of *in vivo* and *in vitro* Treatment with Interferon-α2b on Glycosaminoglycan Production by Dermal Fibroblasts

FIG. 4

| FIBROBLAST | | FIBRONECTIN (ug / 10⁵ CELLS ± SD) | |
|---|---|---|---|
| | | *IN VITRO* | |
| SOURCE | PASSAGE | UNTREATED | IFN-α₂b 10⁵ U/ml |
| KELOID PRE - *IN VIVO* IFN- | 3 | 2.82 ± .01 | 2.91 ± .04 |
| KELOID POST - *IN VIVO* IFN- | 2 | 2.48 ± .15 | 2.41 ± .03 |
| NORMAL SKIN UNTREATED | 2 | 2.71 ± .04 | 2.67 ± .02 |
| KELOID PRE - *IN VIVO* IFN- | 7 | 2.92 ± .02 | 3.16 ± .03 |
| KELOID POST - *IN VIVO* IFN- | 6 | 2.70 ± .04 | 2.78 ± .03 |
| NORMAL SKIN UNTREATED | 6 | 2.92 ± .05 | 3.06 ± .04 |

Table III. Effect of *in vivo* and *in vitro* Treatment with Interferon-α₂b on Fibronectin Production by Dermal Fibroblasts

F I G. 5

| FIBROBLAST SOURCE | P A S S A G E | CELL NUMBER ($\times 10^{-3} / 2 \text{ cm}^2 \pm$ SD) IN VITRO | | | |
|---|---|---|---|---|---|
| | | UNTREATED (DOUBLING TIME IN HRS) | IFN-$\alpha_{2b}$ $10^5$ U/ml | IFN-$\alpha_{2b}$ $10^3$ U/ml | IFN-$\alpha_{2b}$ 10 U/ml |
| KELOID PRE- IN VIVO IFN- | 3 | 51.8 ± 5.2 (42.6) | 19.7 ± 3.3 | 34.3 ± 5.7 | 55.0 ± 6.8 |
| KELOID POST- IN VIVO IFN- | 2 | 49.0 ± 6.4 (43.1) | 22.2 ± 3.6 | 27.5 ± 3.3 | 50.0 ± 7.1 |
| NORMAL SKIN UNTREATED | 2 | 46.8 ± 4.8 (44.2) | 14.7 ± 2.7 | 21.9 ± 3.4 | 49.6 ± 7.2 |

Table IV. Effect of *in vivo* and *in vitro* Treatment with Interferon-$\alpha_{2b}$ on Dermal Fibroblast Proliferation

*FIG. 6*

| FIBROBLAST SOURCE | PASSAGE | COLLAGENASE (mU / $10^5$ CELLS ± SD) IN VITRO | | |
|---|---|---|---|---|
| | | UNTREATED | PERCENT NORMAL | IFN-$\alpha_{2b}$ $10^5$ U/ml |
| KELOID PRE - IN VIVO IFN- | 4 | 7.4 ± 0.6 | 26.7 | 13.1 ± 1.2 |
| KELOID POST - IN VIVO IFN- | 3 | 23.9 ± 1.8 | 96.5 | 31.6 ± 3.1 |
| NORMAL SKIN UNTREATED | 3 | 27.6 ± 2.4 | 100.0 | 37.3 ± 3.4 |
| KELOID PRE - IN VIVO IFN- | 7 | 7.2 ± 0.9 | 31.0 | 11.6 ± 1.0 |
| KELOID POST - IN VIVO IFN- | 6 | 20.1 ± 2.2 | 86.0 | 24.3 ± 2.4 |
| NORMAL SKIN UNTREATED | 6 | 23.2 ± 1.8 | 100.0 | 36.1 ± 3.9 |

Table V. Effect of *in vivo* and *in vitro* Treatment with Interferon-$\alpha_{2b}$ on Collagenase Production by Dermal Fibroblasts

FIG. 8

METHOD OF TREATING FIBROTIC DISORDERS

CROSS REFERENCE TO RELATED APPLICATIONS

This application is a continuation of co-pending application Ser. No. 07/469,149, filed Jan. 24, 1990, now abandoned, which is a continuation-in-part of Ser. No. 07/147,973, filed Jan. 25, 1988, now abandoned.

BACKGROUND OF THE INVENTION

1. Field of the Invention

The present invention relates to methods and compositions for treating fibrotic tissue disorders in human patients.

2. Description of the Prior Art

Tissue fibrosis, characterized by excessive deposition of connective tissue components (most notably collagen) is the major pathological feature in various clinical conditions. The collagen deposition can take place in various internal organs, as in pulmonary fibrosis or liver cirrhosis. Skin is also commonly affected by fibrotic processes, and dermal fibrosis is the clinical pathological hallmark of several acquired and heritable cutaneous disorders.

In most cases, fibrosis is a reactive process, and several different factors can apparently modulate the pathways leading to tissue fibrosis. Such factors, largely elaborated by the inflammatory tissue reaction, include the local expansion of fibroblast subpopulations, immune modulation of the synthetic functions of fibroblasts, and altered regulation of various metabolic reactions governing the biosynthesis and degradation of the connective tissue components. Thus, the net accumulation of collagen in components. Thus, the net accumulation of collagen in fibrosis is a result of imbalance between the factors leading to production and deposition or degradation and removal of collagen.

Although various modalities have been utilized to treat fibrotic diseases and disorders, none of these treatments have been particularly effective because they generally are directed to the symptoms of the disorders but not at the underlying pathology, namely, the imbalance in the metabolic factors regulating production, deposition, degradation and removal of collagen and other connective tissue components. Thus, for example, while topical corticosteroids have been used with some degree of success in treating the early, inflammatory stage of cutaneous keloid formation, such steroid therapy has little or no effect on the later, fibrotic stage when the keloids are actually formed as a result of excess collagen production.

It has been discovered in recent years, however, that activated T-lymphocytes and monocytes/macrophages can effective modulate several fibroblast functions through the release of soluble macromolecular factors, collectively categorized as lymphokines (for the factors released by lymphocytes) and monkines (for the factors released by monocytes such as macrophages). Among the fibroblast functions modulated by these lymphokines and monkines is the production of fibrosis-forming collagen. See, e.g., Duncan, M. R. et al., *J. Invest. Dermatol.*, 83:377 (1984). In 1985, we identified gamma-interferon as the lumphokine an d beta-interferon as the monkine responsible for inhibition of fibroblast collagen production as well as inhibition of late, but not early, fibroblast proliferation. Duncan, M. R. and Berman, B., *J. Exp. Med.*, 162:516–27 (1985).

A number of researchers subsequently studied the effects of gamma-interferon, principally, on collagen production in vitro or in animal models such as mice. E.g., Carlo-Stella et al., *Blood,* 70:1014–19 (1987); Granstein et al., *J. Clin. Invest.*, 79:11254–58 (1987); Sharpe, *Med Hypoth.*, 22:415–19 (1987) Czaja et al., *J. Biol. Chem.*, 262;13348–51 (1987). Some of these researchers suggested that gamma-interferon might be useful in treating fibrotic disorders, but none have conducted published clinical trials with any interferon, nor indicated any specific method for treatment of fibrotic disorders with interferons.

In a paper first published in full in 1987, we disclosed our discovery that a reduced-collagen-producing phenotype in cultured scleroderma fibroblasts persisted after short term exposure to interferons, whether alpha-, beta- or gamma-. Duncan, M. R. and Berman, B., *J. Clin. Invest.*, 79:1318–24 (1987). Notwithstanding that discovery, which was based solely on in vitro data, it was not at all clear whether or which types of interferons would be useful in the treatment of fibrotic tissue disorders in vivo, particularly disorders such as cutaneous keloid formation, scleroderma, progressive systemic sclerosis, and the like, where mere restoration of normal fibroblast collagen production levels may prevent further excess collagen deposition, but will not remove or degrade the fibrotic lesions already formed. Moreover, because of the complexity of the interacting metabolic factors relating to connective tissue matrix formation and degradation, the fact that interferons appeared to cause a persistent inhibition of fibroblast collagen production in vitro by no means proved that a similar effect would be observed in vivo.

Hence, notwithstanding the foregoing discoveries, there has been no method disclosed in the prior art for treating fibrotic tissue disorders in humans in a safe and effective manner to inhibit further fibrotic tissue formation and to reduce or remove entirely already-formed fibrotic lesions.

SUMMARY OF THE INVENTION

It is an object of the present invention to provide a method of treatment of fibrotic tissue disorders in humans which enables both prophylaxis and reversal of such disorders.

It is a further object of the present invention to provide a method of treatment as described above which comprises the administration of a safe and effective pharmacologically active agent to inhibit excess collagen production and induce the degradation of excess connective tissue matrix.

In keeping with the foregoing objects and others which will become apparent hereinafter, the invention resides, briefly stated, in the local or systemic administration to a human patient suffering from a fibrotic tissue disorder of an amount of a composition containing one or more human alpha- or beta interferon sufficient to raise the total concentration of such interferons in the fibrotic tissue area to about 10 to about $4 \times 10^7$ international units (IU) per cubic centimeter. As will be further detailed below, the administration of human alpha- and beta-interferons by suitable methods and in suitable amounts sufficient to raise the concentration in the affected tissue area to the aforementioned concentration range serves the dual purposes of altering the phenotype of excess collagen-producing fibroblasts as well as accelerating the enzymatic degradation of excess connective tissue matrix already deposited. The result, which has been clinically observed, is the inhibition of further fibrotic tissue formation and the removal of existing fibrotic tissue to return the affected area to a normal state.

BRIEF DESCRIPTION OF THE DRAWINGS

FIG. 3 is a table comparing the quantities of extracellular collagen derived from cultures of keloid fibroblasts, pre- and post-in vivo treatment, and normal, untreated fibroblasts. The table also compares collagen production of the same cells after in vitro treatment with interferon-alpha$_{2b}$.

FIG. 4 is a table comparing the quantities of glycosaminoglycans derived from the same in vitro cultures of fibroblasts as in FIG. 3.

FIG. 5 is a table comparing the quantities of fibronectin derived from the same in vitro cultures of fibroblasts as in FIG. 3.

FIG. 6 is a table comparing fibroblast proliferation times in the same in vitro cultures of fibroblasts as in FIG. 3.

FIG. 8 is a table comparing the quantities of collagenase derived from the same in vitro cultures of fibroblasts as in FIG. 3.

DETAILED DESCRIPTION OF THE INVENTION

Figure 1:
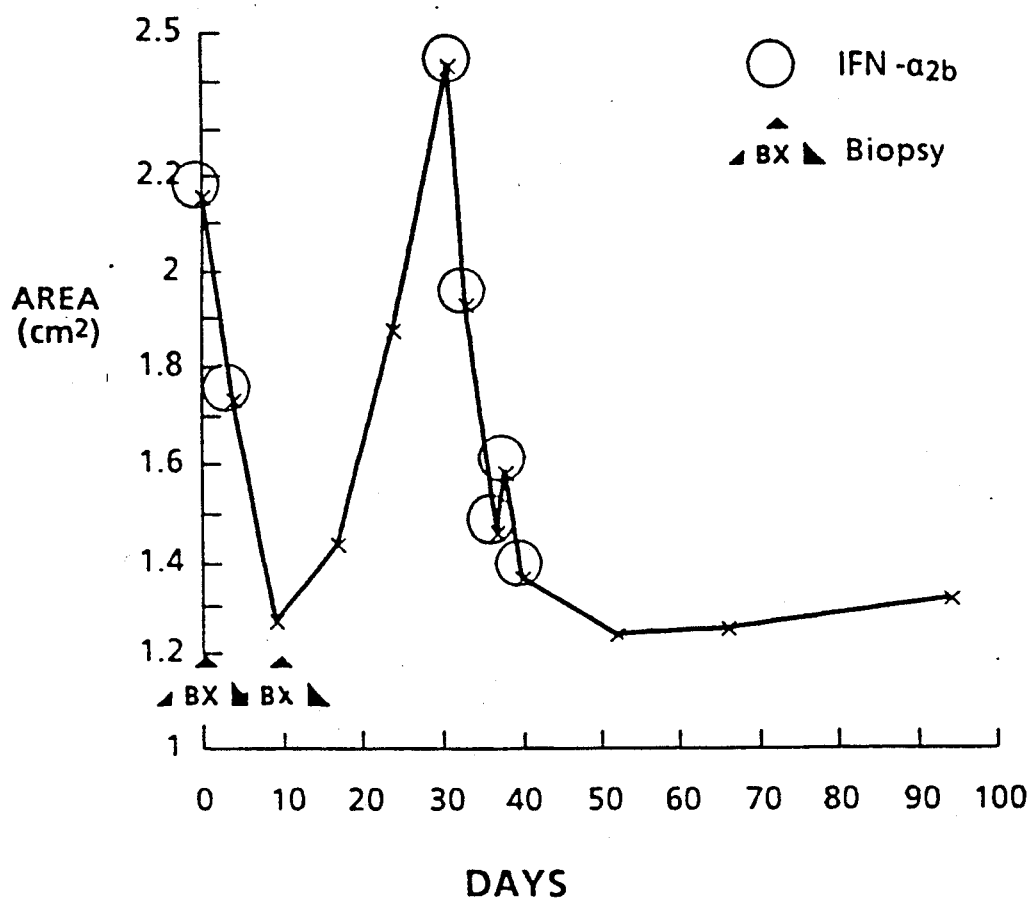
FIG. 1 is a graph showing the variation over time in the lesional area of a keloid treated in accordance with the present invention as specifically detailed in the Example set forth at the end of this specification.

Whereas we had previously disclosed that human interferons acted as persistent fibroblast deactivators, inhibiting both the growth and collagen production of normal fibroblasts and hypercollagen-producing fibroblasts, we have now discovered that human alpha- and bete-interferons (hereinafter referred to as "Type I" interferons) also increase the collagenase activity of the fibroblasts, either by increasing collagenase production to normal levels in diseased fibroblasts or by removing some yet unknown collagenase inhibiting factor. This discovery led to the development of the method of the present invention, which has been found effective in vivo in treating human fibrotic disorders.

The novel method of the present invention comprises the administration to a human patient suffering from a fibrotic tissue disorder of a sufficient amount of a composition containing one or more Type I human interferons to raise the total concentration of Type I interferons in the affected tissue area to about 10 to about $4 \times 10^7$ IU/cc. As used herein, "total concentration of Type I interferons" refers to the combined concentration, expressed in IU/cc, of all Type I human interferons in the tissue area, whether alpha- or beta-interferons, but not gamma (Type II) interferons.

In the case of dermal fibrosis, for example dermal keloids or scleroderma, the desired tissue concentration level may be achieved by injecting the Type I human interferons intralesionally in sufficient quantity to achieve the necessary concentration, based on the size of the lesion. In the case of systemic fibrosis, intramuscular or intravenous routes of administration can be utilized. In the case of pulmonary fibrosis, the interferon can be incorporated into a solution to be administered intrabronchially by means of an inhalator.

In general, the specific method and route of administration selected is dependent on an assessment of the most efficient and quickest method to achieve the necessary interferon concentration at the affected site. The method of the invention is not limited to any specific route of administration, and any conventional method or route of administration known to those skilled in the medical and pharmaceutical arts which achieves the desired tissue concentration of interferon is comprehended by the present invention.

The interferons utilized in the method of the present invention may be naturally derived or recombinant DNA-derived Type I human interferons. Alpha (leukocyte) and beta (fibroblast) interferons, and their subtypes, may be effectively used in the novel treatment methods.

In vitro and clinical data suggest that Type I interferons have much greater utility in vivo than Type II interferons because of their greater and more consistent activity in increasing fibroblast collagenase production, among a number of other factors. Human recombinant DNA-derived alpha$_{2b}$-interferon has been shown particularly effective in vivo.

Despite suggestions in recent literature that gamma-interferons might be effective in treating various fibrotic manifestations in humans, it now appears that the utility of these Type II interferons may be negligible in comparison with the Type I interferons. The two different groups of interferons differ markedly in many respects, including their chemical structures and biological characteristics, for example the receptors to which they bind and the chromosomes on which they are encoded.

Clinically, it has been observed that Type I interferons promote significant reduction in fibrotic lesions such as keloids without untoward adverse effects. Type II interferons, on the other hand, are not of practical value in reducing keloids——they increase fibroblast glycosaminoglycan and fibronectin synthesis while not consistently increasing collagenase production, and can cause erosion of the dermis over treated keloid sites. The substantial clinical superiority of the Type I interferons in treating fibrotic disorders was a surprising discovery in view of the prior art indications of in vitro collagen-inhibiting activity for both interferon types.

The interferon composition administered according to the present invention may comprise one or more Type I human interferons, whether of natural origin or recombinant DNA-derived, in any pharmaceutically acceptable vehicle suitable for the treatment of a particular condition. Thus, if a parenteral route of administration is required, a suitable injectable solution of human interferons may be prepared by any conventional means known in the pharmaceutical arts. For example, such as injectable solution may comprise sterile isotonic saline, preservatives such as methylparaben or propylparaben, pH adjusters, buffers, and the like. Similarly, any standard vehicle known in the art to be suitable for inhalation agents may be utilized to create a vehicle in which the interferons may be administered as a nebulized spray from an inhaler, e.g., for treatment of pulmonary fibrosis. Compatible emulsifiers, dispersing agents, wetting agents and the like may also be present.

A wide variety of suitable parenteral and inhalant vehicles are set forth in the standard text entitled "*Remington's Pharmaceutical Sciences*" (17th ed. 1985). The invention is not limited to any particular vehicle or formulation for the interferon compositions administered. It is only necessary that the vehicle be compatible with Type I human interferons and one in which the interferons may be easily dissolved or dispersed.

The method of the present invention is useful in treating any fibrotic disorder in humans characterized by excessive fibroblast production of connective tissue matrix, including collagen, fibronectin and glycosaminoglycans (GAG). This includes, among others, the following disorders:

- cutaneous keloid formation
- progressive systemic sclerosis (PSS)
- liver cirrhosis
- idiopathic and pharmacologically induced pulmonary fibrosis
- chronic graft versus-host disease
- scleroderma (local and systemic)
- Peyronie's disease
- pharmacologically induced fibrosis of the penis
- post-cystoscopic urethral stenosis
- post-surgical internal adhesions
- idiopathic and pharmacologically induced retroperitoneal fibrosis
- myelofibrosis To treat each of the above disorders, it is necessary only to administer a sufficient quantity of a composition containing one or more Type I human interferons, whether naturally derived or recombinant DNA-derived, to raise the total tissue concentration of such interferons in the affected area to about 10 to about $4\times10^7$ IU/cc. A preferred range of tissue concentrations of Type I interferons is from about $10^3$ to about $10^7$ IU/cc. Administration of the interferon composition by any appropriate route and incorporating any preferred vehicle may be repeated as often as deemed necessary to achieve the therapeutic goal of restoration of normal fibroblast function and degradation of fibrotic lesions. In each instance, however, the administration of the interferon composition should raise the total tissue concentration of Type I interferons in the affected area to the range specified above.

The dosage amounts of Type I interferon administered to achieve the desired concentration in the affected tissue area will generally be higher when systemic routes of administration are utilized, as opposed to local administration, because upon sytemic administration the interferons will be diluted and metabolized to some degree before reaching the fibrotic site. The determination of dosage amounts of interferon on a case-by-case basis to achieve the desired tissue concentration levels is within the skill of those knowledgable in the medical and pharmaceutical arts.

As set forth in greater detail in the following Example, the method of the present invention was found clinically effective in the treatment of a progressively enlarging cutaneous keloid. After only two intralesional injections of a composition containing a Type I interferon, the lesional area was reduced by 41%. Moreover, fibroblasts cultured from the keloid prior to and after interferon injection were compared with fibroblasts cultured from the patient's normal skin, revealing that while pre-interferon fibroblasts produced more collagen, more glycosaminoglycans and less collagenase than the patient's own normal fibroblasts, the post-interferon fibroblasts persistently produced normal or subnormal amounts of collagen and glycosaminoglycans and exhibited normalized levels of collagenase activity. The result of the interferon treatment was, thus, not only cessation of fibrotic tissue production but reduction of the already existing fibrotic lesion through the normalization of collagenase.

The following Example provides a detailed illustration of the method according to the present invention for treating fibrotic disorders in humans. The Example is not intended, however, to limit or restrict the scope of the invention or the nature of the conditions for which the invention is indicated in any way. Moreover, the Example should not be construed as providing dosage amounts or regiments, routes of administration or specific vehicles for the human interferons which must be utilized exclusively in order to practice the present invention.

EXAMPLE

Patient Treatment

A 55 year old man with a history of post surgical cutaneous keloid formation developed a keloid in a site on his upper right arm 10 weeks after receiving 200 $W/cm^2$ as a test dose prior to planned $CO_2$ laser ablation of his cafe-au-lait macule. The untreated lesion was biopsied under 1% lidocaine local anesthesia before interferon treatment (pre-IFN) and then injected with 1.5 million IU IFN-alpha$_{2b}$ in 0.15 ml of solution using a 30-gauge needle immediately and 5 days later. On the 9th day the keloid was biopsied (post-IFN) as was normal appearing skin in a corresponding anatomical site. The keloid was further injected with 1.5 million IU IFN-alpha$_{2b}$ in 0.15 ml on days, 31, 33, 37, 38 and 40. Lesional area was calculated gravimetrically from lesional outlines drawn on plastic.

Interferons

The patient's keloid received intralesional injections (1.5 million IU/injection) of recombinant DNA-derived human IFN-alpha$_{2b}$ (Intro A; Schering Corporation, Kenilworth, N.J.). Recombinant DNA-derived human IFN-alpha$_{2b}$ (SCH 30500) used in the in vitro studies described herein was produced in *Escherichia coli* and supplied by the Schering Corporation, Kenilworth, N.J. This IFN$_{2b}$ preparation ($6.6\times10^7$ IU/ml of phosphate buffered saline; specific activity of $1.2\times10^8$ IU/mg protein) was added directly to fibroblast cultures after dilution to desired concentrations with Dulbecco's modified Eagle's medium (DME) containing 0.1% human serum albumin.

Fibroblast Cultures

Primary fibroblast cultures were initiated from full thickness 2 mm punch biopsies using an explant method. The explants were cultured in 24 well microculture plates (2 $cm^2$ surface area; Linbro: Flow Labs, McLean Va.) in DME containing 25 mM Hepes, 2 mM glutamine, 100 IU/ml penicillin and 100 μg/ml streptomycin plus 20% heat-activated fetal calf serum (FCS) (Whittake-MA Bioproducts, Walkersville, Ma.) at 37° C. in 5% $CO_2$ humidified atmosphere. These primary fibroblast cultures approached confluency after 36 to 42 days of growth and were subsequently trypsinized and subcultured in DME+20% FCS with subpassage at weekly intervals. Fibroblasts from selected subcultures were then assayed for functional activity, namely, fibroblast growth, collagen production, glycosaminoglycan (GAG) production, fibronectin production and collagenase production.

Clinical Response

As shown in FIG. 1, the keloid injected intralesionally with IFN-alpha$_{2b}$ on days 0 and 4 rapidly reduced in area by 41% by day 9 at which time a post-IFN biopsy of the keloid was performed. In light of the rapid increase in the area of the keloid which peaked on day 31, 5 additional IFN-alpha$_{2b}$ doses were injected intralesionally during the subsequent 9 days. These treatments again resulted in a rapid, persistent reduction in lesional area (46% at day 94). Qualitatively, following each set of injections, the keloid became markedly softer and less raised. The patient experienced transient myalgias, which required no treatment, following the initial set of injections.

In Vitro Production of Matrix Components By Keloidal and Normal Fibroblasts

Figure 2:
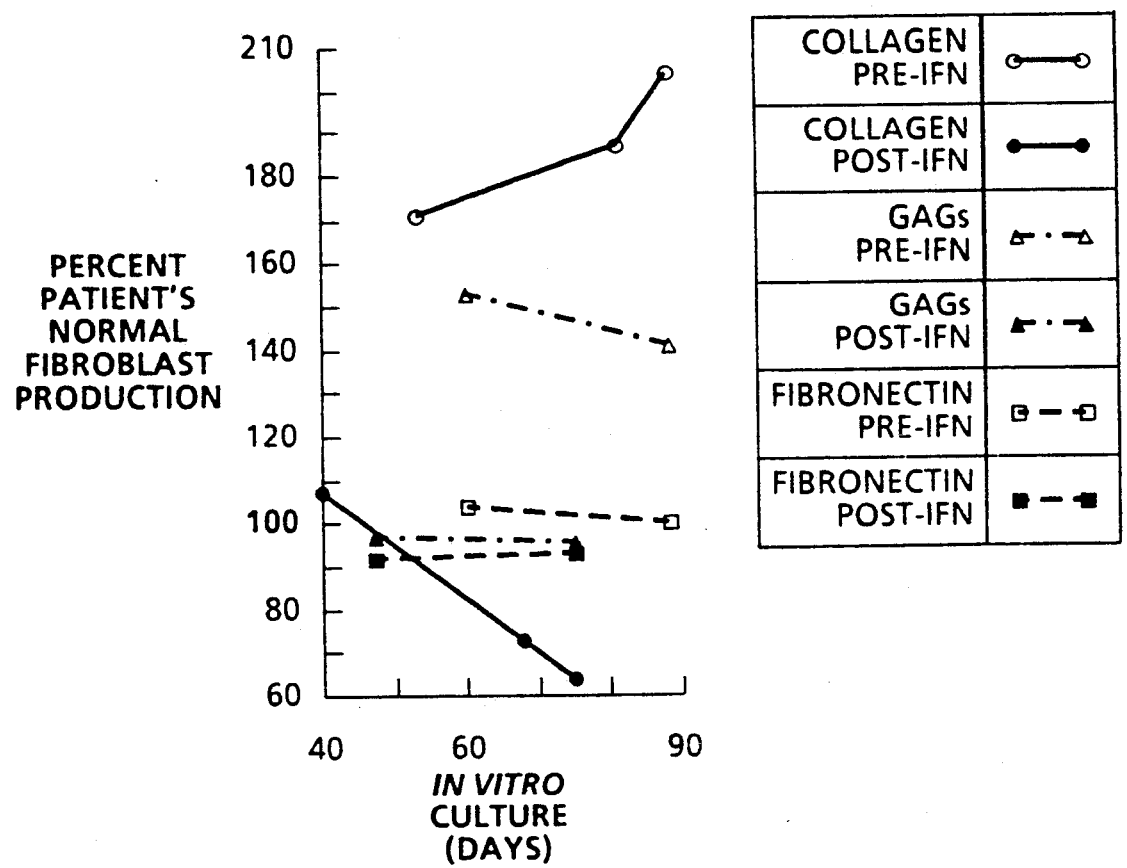
FIG. 2 is a graph showing variation over time in the production of various connective tissue matrix factors by keloid fibroblasts before and after in vivo treatment in accordance with the present invention, expressed as a percentage of normal fibroblast production of those factors.

As summarized in FIG. 2, pre-IFN keloidal fibroblasts in vitro displayed an activated phenotype characterized by persistent hypercollagen and hyper-GAG production compared to the patient's normal fibroblasts. The initial set of IFN-alpha$_{2b}$ injections in vivo resulted in a persistent de-activation of the keloidal fibroblast pheno-type, with post-IFN keloidal fibroblasts producing normal or sub-normal amounts of collagen and GAGs. This persistent de-activation was selective, as the normal level of pre-IFN keloidal fibroblast production of fibronectin, another component of connective tissue matrix, remained normal in post-IFN keloidal fibroblasts. As detailed in Tables I and II (FIGS. 3 and 4), the addition of IFN-alpha$_{2b}$ to confluent cultures of pre-IFN keloidal, post-IFN keloidal or normal fibroblasts resulted in a dose-related reduction in collagen and GAG production. Interestingly, a concentration range of $10^3$–$10^5$ IU/ml, which theoretically is attainable locally in vivo, normalized the otherwise persistent hypercollagen and hyper-GAG production by pre-IFN keloidal fibroblasts. As shown in Table III (FIG. 5), in vitro exposure of different passages of any of the 3 fibroblast lines to IFN-alpha$_{2b}$ ($10^5$ IU/ml) failed to alter their normal level of fibronectin production.

In Vitro Proliferation of Keloidal and Normal Fibroblasts

The observed effects of in vivo IFN-alpha$_{2b}$ on in vitro functions of keloidal fibroblasts were not secondary to an antiproliferative effect. Confluent non-proliferating cultures were examined, and as shown in Table IV (FIG. 6), in vivo exposure to IFN-alpha2$_b$ failed to exert any lasting effect on proliferation, with the doubling time of pre-IFN, post-IFN and normal fibroblasts being virtually identical (p>0.5). It is likely that, similar to its effect in vitro (Table IV), exposure to IFN-alpha$_{2b}$ inhibits fibroblast proliferation in vivo, but its continued presence may be required.

Figure 7:
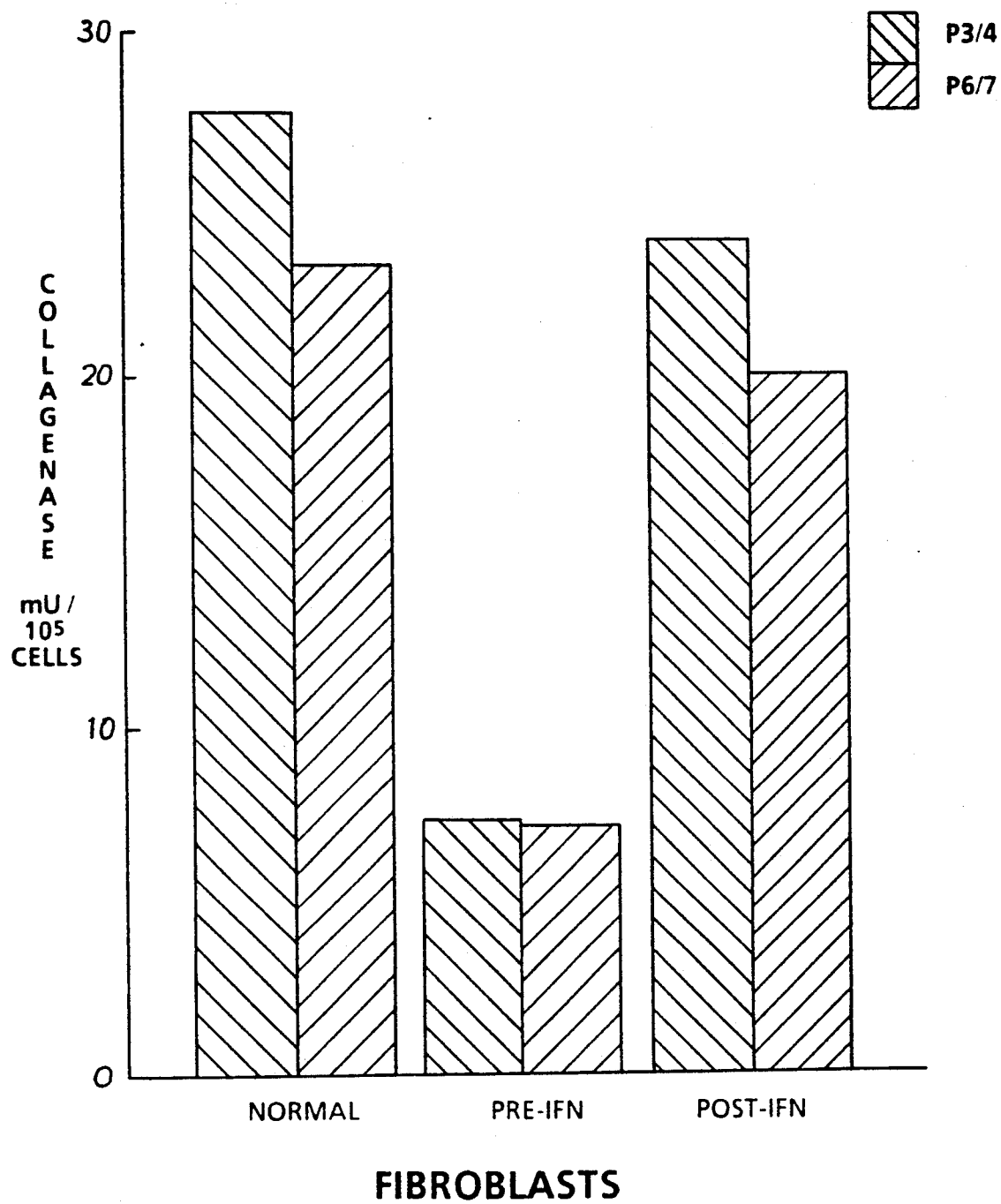
FIG. 7 is a bar graph illustrating the comparative amounts of collagenase derived from in vitro cultures of keloid fibroblasts pre- and post-in vivo-treatment, and normal, untreated fibroblasts.

In Vitro Elaboration of Collagenase Activity By Keloidal and Normal Fibroblasts Although our detection of a persistent reduction of collagen and GAG production by keloidal fibroblasts exposed in vivo to INF-a$_{2b}$ could ultimately result in an antifibrotic effect, it was important to examine the potential catabolic activity of such fibroblasts on pre-formed collagen, especially in light of the rapid clinical response (FIG. 1). As shown in FIG. 7 keloidal fibroblasts elaborate less than ⅓ the normal amount of collagenase activity, which combined with their hyper-collagen and GAG production could result in the development of a keloid. Interestingly, in vivo exposure to IFN-alpha$_{2b}$ normalized the collagenase activity elaborated by keloidal fibroblasts. This in vitro effect was persistent, being detected in early and late cell passages, in the absence of exogenous IFN. As shown in Table V (FIG. 8), in vitro exposure of each of the 3 fibroblast lines to IFN-alpha$_{2b}$ ($10^5$ IU/ml) increased the level of elaborated collagenase activity.

It has thus been shown that there are provided methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims:

1. A method of treating a human patient suffering from cutaneous keloid formation in a tissue area to reduce and degrade the keloid lesions comprising the administration to the patient of a composition containing a human alpha$_{2b}$-interferon to raise the total concentration of such interferon in the tissue area to 10 to $4 \times 10^7$ international units per cubic centimeter.

2. A method according to claim 1 wherein said interferon is naturally derived or recombinant DNA-derived.

3. A method according to claim 2 wherein said interferon is recombinant DNA-derived.

4. A method according to claim 1 where said composition is administered via an intralesional or intramuscular injection, an intravenous injection or infusion, or an intrabronchial inhalant solution.

5. A method according to claim 4 wherein said composition is injected intralesionally.

6. A method according to claim 1 wherein the total concentration of said interferon in the tissue area is from $10^3$ to $10^7$ international units per cubic centimeter.

7. A method according to claim 1 wherein said composition comprises about 1.5 million international units of recombinant DNA-derive human alpha$_{2b}$-interferon in 0.15 ml of solution.

8. A method according to claim 11 wherein said composition is injected intralesionally.

9. A method according to claim 1 wherein said composition comprises a pharmaceutically acceptable injectable solution of said interferon.

10. A method according to claim 1 wherein the administration of said composition is repeated as necessary until cessation of fibrotic tissue production and reduction of fibrotic lesion is achieved.

* * * * *